United States Patent
Liu et al.

(10) Patent No.: US 9,981,917 B2
(45) Date of Patent: May 29, 2018

(54) PREPARATION METHOD FOR REVAPRAZAN HYDROCHLORIDE

(71) Applicant: JIANGSU TASLY DIYI PHARMACEUTICAL CO., LTD., Jiangsu (CN)

(72) Inventors: Wenzheng Liu, Jiangsu (CN); Guocheng Wang, Jiangsu (CN); Qingwei Hou, Jiangsu (CN); Qiaoping Cui, Jiangsu (CN); Zhanyuan Zhu, Jiangsu (CN); Jinping Liu, Jiangsu (CN); Mingbo Yang, Jiangsu (CN); Hongguang Meng, Jiangsu (CN)

(73) Assignee: Jiangsu Tasly Diyi Pharmaceutical Co., Ltd., Jiangsu (CN)

( * ) Notice: Subject to any disclaimer, the term of this patent is extended or adjusted under 35 U.S.C. 154(b) by 0 days. days.

(21) Appl. No.: 15/519,886

(22) PCT Filed: Nov. 12, 2015

(86) PCT No.: PCT/CN2015/094462
§ 371 (c)(1),
(2) Date: Apr. 18, 2017

(87) PCT Pub. No.: WO2016/078542
PCT Pub. Date: May 26, 2016

(65) Prior Publication Data
US 2017/0267646 A1    Sep. 21, 2017

(30) Foreign Application Priority Data
Nov. 19, 2014  (CN) .......................... 2014 1 0665839

(51) Int. Cl.
| | | |
|---|---|---|
| *C07D 401/04* | (2006.01) | |
| *C07D 239/08* | (2006.01) | |
| *C07D 239/22* | (2006.01) | |
| *A61K 31/5395* | (2006.01) | |
| *C07D 217/00* | (2006.01) | |

(52) U.S. Cl.
CPC ........ *C07D 239/08* (2013.01); *A61K 31/5395* (2013.01); *C07D 217/00* (2013.01); *C07D 239/22* (2013.01); *C07D 401/04* (2013.01)

(58) Field of Classification Search
CPC ................................. C07D 401/04
See application file for complete search history.

(56) References Cited

U.S. PATENT DOCUMENTS

| | | |
|---|---|---|
| 5,750,531 A | 5/1998 | Lee et al. |
| 5,990,311 A | 11/1999 | Hong et al. |

FOREIGN PATENT DOCUMENTS

| | | |
|---|---|---|
| CN | 1217722 A | 5/1999 |
| WO | 9605177 A1 | 2/1996 |
| WO | 9818784 A1 | 5/1998 |
| WO | 2014060908 A1 | 4/2014 |

OTHER PUBLICATIONS

Ding, Bing, "Study on the Synthesis of the Reversible Proton Pump Inhibitor Revaprazan Hydrochloride", Medicine & Public Health, China Master's Theses Full-Text Database, Jul. 31, 2010 (Jul. 31, 2010) p. 16, section 2.5 and pp. 37-39, section 5.3 (translation of pertinent section only provided).
Song, Wei-guo et al., "A New Method for Preparing Revaprazan Hydrochloride", Chinese Journal of New Drugs 2013, 22(14), 1694-1696 (translation of pertinent section only provided).
Sun, Zheng-jin et al., "Synthesis of Revaprazan Hydrochloride", Chinese Journal of Pharmaceuticals, vol. 39, No. 5, May 31, 2008 (May 31, 2008), see the whole document (translation of pertinent section only provided).
Jiang, Jun-rong et al., "Synthesis of Revaprazan"; Journal of Synthetic Chemistry 2008, 16(4), 490-492 (translation of pertinent section provided).
Ding, Bing et al; "Synthesis of 4-hydroxy-2-(4-fluoroanilino)-5,6-dimethylpyryimidine"; Journal of Guongdong Pharmaceutical University, Apr. 2009, 25(2), 173-174 (translation of pertinent section provided).
Merck Indexing of Revaprazan Hydrochloride, 2013 last revised.
International Search Report from International Application No. PCT/CN2015/094462 dated Feb. 16, 2016.

*Primary Examiner* — Deepak R Rao
(74) *Attorney, Agent, or Firm* — Dilworth & Barrese, LLP

(57) ABSTRACT

Provided is a preparation method for revaprazan hydrochloride, the method comprising: (1) the preparation of 4-hydroxyl-2-(4-fluoroaniline)-5,6-dimethylpyrimidine; (2) the preparation of 4-chloro-2-(4-fluoroaniline)-5,6-dimethylpyrimidine; (3) the preparation of revaprazan hydrochloride. The method has advantages such as simple operations, high product purity, good yield and suitability for industrial production.

30 Claims, 1 Drawing Sheet

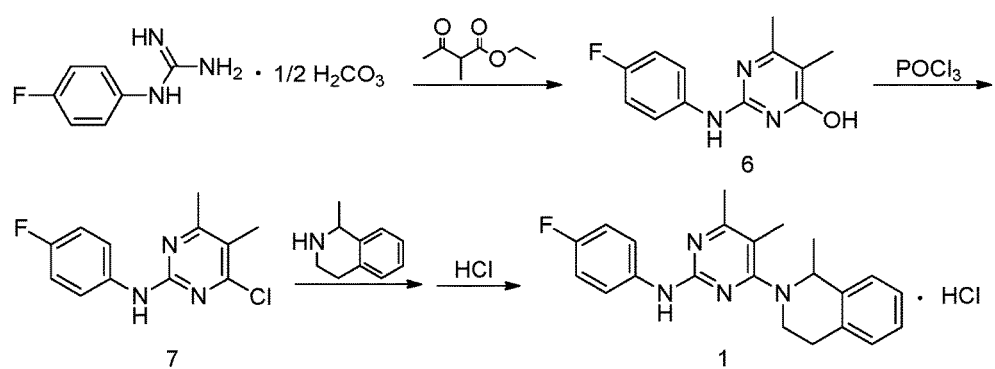

PREPARATION METHOD FOR REVAPRAZAN HYDROCHLORIDE

TECHNICAL FIELD

The present invention relates to the field of medicine, and particularly relates to a preparation method for revaprazan hydrochloride.

BACKGROUND ART

The chemical name of revaprazan hydrochloride is 2-(4-fluoroaniline)-4-(1-methyl-1,2,3,4-tetrahydroisoquinoline-2-yl)-5,6-dimethylpyrimidine hydrochloride. In 1995, South Korea disclosed that the compound had an excellent anti-secretory activity, and revaprazan hydrochloride was approved by South Korea FDA in 2007 for the treatment of duodenal ulcer and gastritis. As a new generation of reversible proton pump inhibitor and only marketed potassium competitive acid pump inhibitor worldwide, much attention was given to this drug. There have been reports of synthetic process routes in succession since its debut, so far there are three main synthetic process routes for revaprazan hydrochloride:

Method 1, the method disclosed in patent WO9605177 had the synthetic route as follows:

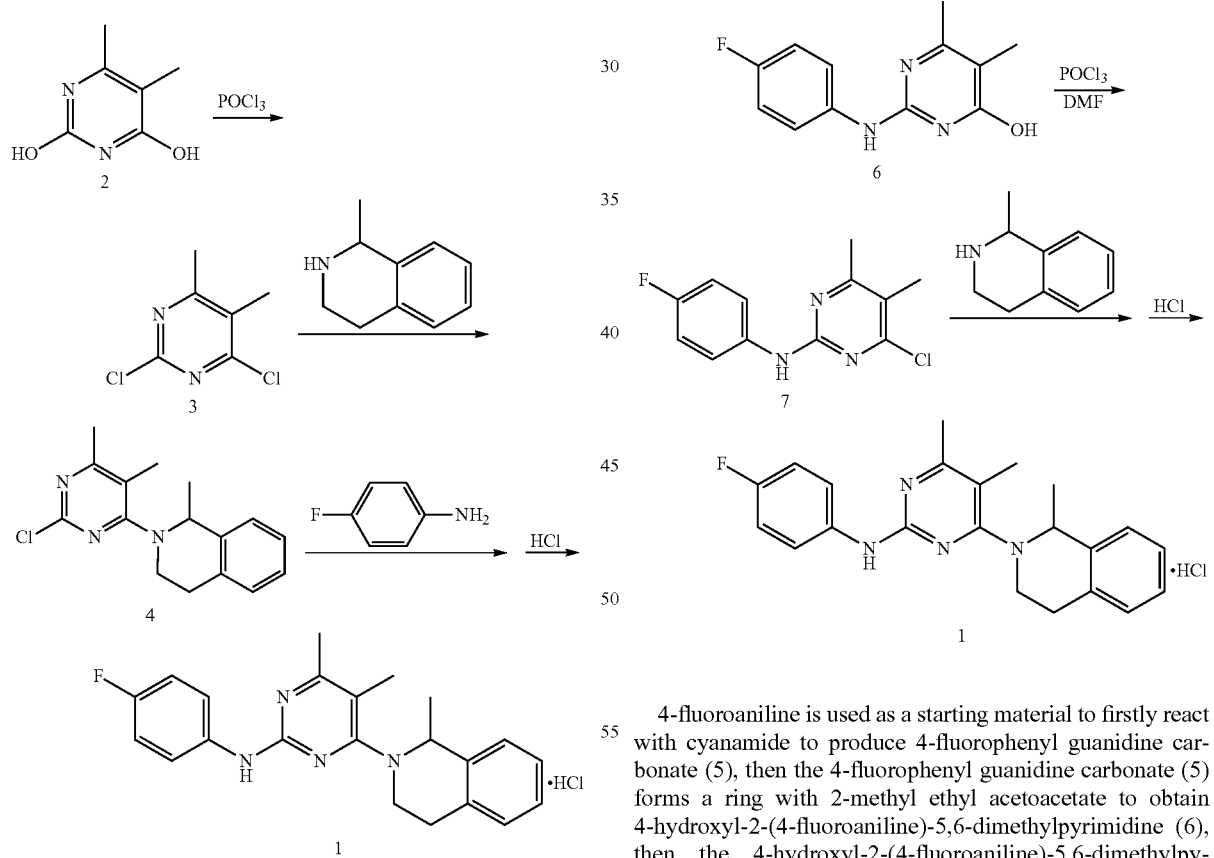

2,4-dihydroxyl-5,6-dimethylpyrimidine (2) is used as a raw material to react with phosphorus oxychloride to produce 2,4-dichloro-5,6-dimethylpyrimidine (3), then the 2,4-dichloro-5,6-dimethylpyrimidine (3) is subjected to alkylation reaction with 1-methyl-1,2,3,4-tetrahydroisoquinoline to produce 2-chloro-4-(1-methyl-1,2,3,4-tetrahydroisoquinoline-2-yl)-5,6-dimethylpyrimidine (4), the 2-chloro-4-(1-methyl-1,2,3,4-tetrahydroisoquinoline-2-yl)-5,6-dimethyl-pyrimidine (4) is subjected to alkylation reaction with 4-fluoroaniline, salt is formed by hydrochloric acid, and revaprazan hydrochloride is obtained. Since the method has a location selectivity problem during the reaction process of intermediate (3) with 1-methyl-1,2,3,4-tetrahydroisoquinoline, the yield is low and its application restrained.

Method 2, the method disclosed in patent WO9818784 had the synthetic route as follows:

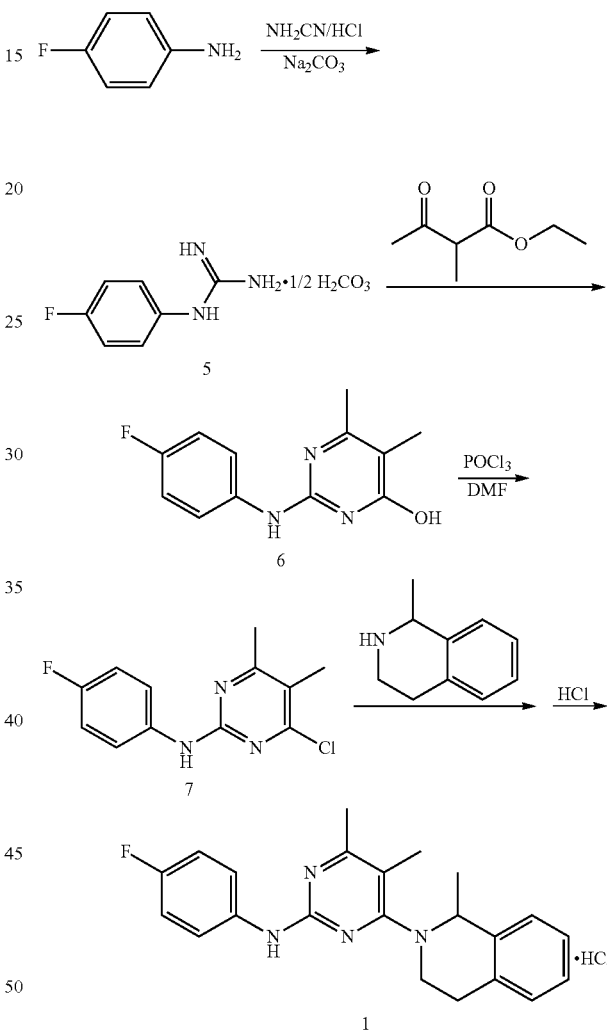

4-fluoroaniline is used as a starting material to firstly react with cyanamide to produce 4-fluorophenyl guanidine carbonate (5), then the 4-fluorophenyl guanidine carbonate (5) forms a ring with 2-methyl ethyl acetoacetate to obtain 4-hydroxyl-2-(4-fluoroaniline)-5,6-dimethylpyrimidine (6), then the 4-hydroxyl-2-(4-fluoroaniline)-5,6-dimethylpyrimidine (6) reacts with phosphorus oxychloride to obtain 4-chloro-2-(4-fluoroaniline)-5,6-dimethylpyrimidine (7), then the 4-chloro-2-(4-fluoroaniline)-5,6-dimethylpyrimidine (7) reacts with 1-methyl-1,2,3,4-tetrahydroisoquinoline to obtain revaprazan, finally salt is formed by hydrogen chloride to obtain the final product of revaprazan hydrochloride.

Method 3: the method disclosed by *Chinese Journal of New Drugs* 2013, 22 (14), 1694-1696 had the synthetic route as follows:

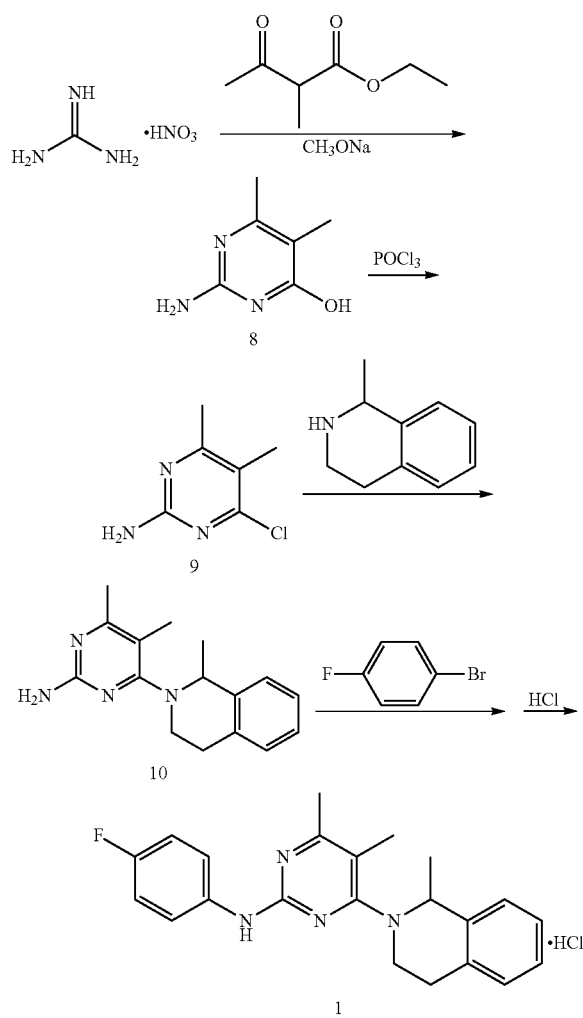

guanidine nitrate is used as a starting material to cyclize with 2-methyl ethyl acetoacetate in the presence of sodium methylate to produce 2-amino-4-hydroxyl-5,6-dimethylpyrimidine (8), then the 2-amino-4-hydroxyl-5,6-dimethylpyrimidine (8) is subjected to chlorination with phosphorus oxychloride to produce a product, the product reacts with 1-methyl-1,2,3,4-tetrahydroisoquinoline to produce 2-amino-4-(1-methyl-1,2,3,4-tetrahydroisoquinoline-2-yl)-5,6-dimethylpyrimidine (10), the 2-amino-4-(1-methyl-1,2,3,4-tetrahydroisoquinoline-2-yl)-5,6-dimethylpyrimidine (10) finally reacts with 4-bromo-fluorobenzene to produce revaprazan, and salt is formed by introducing hydrogen chloride to obtain the revaprazan hydrochloride, because the process needs to evaporate off phosphorus oxychloride, acetic anhydride and the like, so the industrial production is limited. By comparing these three process routes, the method disclosed by patent WO9818784 has stronger specificity. *Synthetics Chemistry* 2008, 16 (4), 490-2; *Chinese Journal of Industrial Medicine* 2008, 39 (5), 321-324; *Journal of Guangdong Pharmaceutical University*, 2009, 25 (2), 173-174, etc. all use the process route, and optimize it.

However, there are various limitations. For example, during the preparation of 4-hydroxyl-2-(4-fluoroaniline)-5,6-dimethylpyrimidine (6), reflux reaction was performed in DMF in the WO9818784 and *Synthetics Chemistry*, isopropanol was added after reaction, and the yield was just 61.4%. In both the *Chinese Journal of Industrial Medicine* and the *Journal of Guangdong Pharmaceutical University*, 4-fluorophenyl guanidine carbonate firstly reacted with sodium methoxide or sodium ethoxide, and then formed ring with 2-methyl ethyl acetoacetate in the presence of pyridine; after reaction, and hydrochloric acid was added to adjust pH to 7 to obtain the intermediate (6). During the preparation of 4-chloro-2-(4-fluoroaniline)-5,6-dimethylpyrimidine (7), WO9818784, *Synthetics Chemistry* and *Chinese Journal of Industrial Medicine*, all raw materials were poured into DMF, and phosphorus oxychloride was dropwise added at 80-85° C.; ice-water was added after reaction, and pH was adjusted to 10 or above 10 with sodium hydroxide. Because a large amount of phosphate was mixed in the products, the quality of intermediates was affected. In the preparation process of revaprazan hydrochloride, in literatures, ethylene glycol and n-butanol were used as the solvent to react at 130° C. for about 30 hours in the presence of triethylamine. Acetone was continued to add after reaction, then water was added. The resulting mixture was stirred for 2 hours, filtered to obtain the solid, and the solid was dissolved in dichloromethane to wash with acid and alkaline, dry, and concentrate the dichloromethane layer. The residue was added with ethanol for dissolution and salt was formed by introducing hydrogen chloride or adding hydrochloric acid. The synthetic process had problems of long reaction time, complicated post-processing and the like.

SUMMARY OF THE INVENTION

In order to solve above-mentioned technical problems, the present invention provides a preparation method of revaprazan hydrochloride, which is easy to industrialize and has high yield.

The present invention is realized through the following technical scheme:

The characteristic of the present invention is that in the preparation process of 4-hydroxyl-2-(4-fluoroaniline)-5,6-dimethylpyrimidine (6), the 4-fluorophenyl guanidine carbonate and 2-methyl ethyl acetoacetate are heated for dehydration in a solvent until the raw materials are completely reacted, then obtaining 4-hydroxyl-2-(4-fluoroaniline)-5,6-dimethylpyrimidine (6).

The characteristic of the present invention is that in the preparation process of 4-chloro-2-(4-fluoroaniline)-5,6-dimethylpyrimidine (7), the 4-hydroxyl-2-(4-fluoroaniline)-5,6-dimethylpyrimidine (6) and phosphorus oxychloride are heated in a solvent until the raw materials are completely reacted, then obtaining 4-chloro-2-(4-fluoroaniline)-5,6-dimethylpyrimidine (7).

The characteristic of the present invention is that in the preparation process of revaprazan hydrochloride, 4-chloro-2-(4-fluoroaniline)-5,6-dimethylpyrimidine (7) and 1-methyl-1,2,3,4-tetrahydroisoquinoline are heated in a solvent with or without base until the raw materials are completely reacted, then obtaining revaprazan hydrochloride.

The specific method is present as follows:
A preparation method of revaprazan hydrochloride of the present invention comprises the following steps:
(1) preparation of 4-hydroxyl-2-(4-fluoroaniline)-5,6-dimethylpyrimidine: adding the 4-fluorophenyl guanidine carbonate and 2-methyl ethyl acetoacetate in a reactor, adding the solvent, carrying out reflux dehydration by heating with or without base (or strong base salt) until the raw materials are completely reacted, cooling, adding water and stirring, filtering, washing with water, then obtaining 4-hydroxyl-2-(4-fluoroaniline)-5,6-dimethylpyrimidine;

(2) preparation of 4-chloro-2-(4-fluoroaniline)-5,6-dimethylpyrimidine: the 4-hydroxyl-2-(4-fluoroaniline)-5,6-dimethylpyrimidine (6) and phosphorus oxychloride are heated and refluxed in a solvent until the raw materials are completely reacted, cooling, adding water, directly separating the liquid or separating the liquid after adjusting the pH with base, extracting the water layer with solvent, combining the organic layers, and washing the organic layers with water until they are neutral, and concentrating the organic layer, then obtaining 4-chloro-2-(4-fluoroaniline)-5,6-dimethylpyrimidine;

(3) preparation of revaprazan hydrochloride: the 4-chloro-2-(4-fluoroaniline)-5,6-dimethylpyrimidine (7) and 1-methyl-1,2,3,4-tetrahydroisoquinoline or its hydrochloride salt are heated in a solvent until the raw materials are completely reacted, adding ethanol and hydrochloric acid, and filtering, then obtaining revaprazan hydrochloride.

Or adding base into the 4-chloro-2-(4-fluoroaniline)-5,6-dimethylpyrimidine (7) and 1-methyl-1,2,3,4-tetrahydroisoquinoline, heating in a solvent for reaction, after reaction, when it is slightly cold, adding water and dichloromethane in the reaction solution, stirring, separating out water layer, and extracting the water layer with dichloromethane, washing the combined dichloromethane layer with dilute hydrochloric acid and water, concentrating the dichlormethane layer, dissolving the residues into ethanol, adding hydrochloric acid for adjusting pH to 1, stirring and carrying out crystallization, then obtaining revaprazan hydrochloride.

The reaction of preferably the above steps (1)-(3) can also be carried out under the protection of gas, and the gas is argon or nitrogen, preferably nitrogen.

The reaction with base is preferred in the step (1) of the present invention, wherein the molar ratio of 4-fluorophenyl guanidine carbonate to 2-methyl ethyl acetoacetate to base is 1:1-2:0-2, preferably 1:1.2-1.6:0.5-1.

The reaction without base can be also performed in the step (1) of the present invention, wherein the molar ratio of 4-fluorophenyl guanidine carbonate to 2-methyl ethyl acetoacetate is 1:1-2, preferably 1:1.2-1.6.

The base or strong base salt of the above step (1) includes, but is not limited to one or more of sodium hydroxide, potassium hydroxide, barium hydroxide, lithium hydroxide, sodium carbonate, potassium carbonate, lithium carbonate, sodium methoxide or sodium ethoxide, and preferably sodium hydroxide and potassium hydroxide.

The 4-fluorophenyl guanidine carbonate of the above step (1) is 4-fluorophenyl guanidine carbonate (F—$C_6H_4$NHC($NH_2$)NH.$H_2CO_3$) (1:1) or 4-fluorophenyl guanidine carbonate (1:0.5) (F—$C_6H_4$NHC($NH_2$)NH.½$H_2CO_3$) preferably 4-fluorophenyl guanidine carbonate (1:0.5) (F—$C_6H_4$NHC($NH_2$)NH.½$H_2CO_3$) that is 4-fluorophenyl guanidine carbonate (5).

The solvent of the above step (1) is selected from one or more of toluene, xylene, benzene, chlorobenzene and cyclohexane, preferably toluene. The feeding ratio by weight is 1:2-20, preferably 1:4-8. The feeding ratio by weight is the weight ratio of 4-fluorophenyl guanidine carbonate to solvent.

The feeding molar ratio of the 4-hydroxyl-2-(4-fluoroaniline)-5,6-dimethylpyrimidine (6) to phosphorus oxychloride of the above step (2) is 1:0.5-2, preferably 1:0.6-1.0.

The solvent described in step (2) includes, but is not limited to one or more of toluene, xylene, benzene, chlorobenzene, cyclohexane, n-hexane and DMF (dimethylformamide), and the toluene or xylene is preferred. The feeding ratio by weight is 1:2-20, and 1:3-8 is preferred. The feeding ratio by weight refers to the weight ratio of 4-hydroxyl-2-(4-fluoroaniline)-5,6-dimethylpyrimidine (6) to the solvent.

In order to separate a product more easily, after the reaction of raw materials is completed in step (2), a base preferably used to adjust pH and then liquid is separated.

The base described in above-mentioned step (2) includes, but is not limited to one or more of sodium hydroxide, potassium hydroxide and barium hydroxide, and sodium hydroxide is preferred; the base is used to adjust pH to 1-10, and 2-7 is preferred.

Another case in step (2) of the present invention includes: when the solvent in heating reaction is polar solvent such as DMF, non-polar solvent such as toluene needs to be added after reaction, then water is added; the base is used to adjust pH to 1-10, and 2-7 is preferred.

The preparation of revaprazan hydrochloride in step (3) of the present invention is divided into the following two cases.

Method 1. The 4-chloro-2-(4-fluoroaniline)-5,6-dimethylpyrimidine (7) and 1-methyl-1,2,3,4-tetrahydroisoquinoline or hydrochloride thereof are heated to react in the solvent, after the reaction, ethanol and hydrochloric acid are added to obtain revaprazan hydrochloride, wherein, the feeding molar ratio of 4-chloro-2-(4-fluoroaniline)-5,6-dimethylpyrimidine (7) to 1-methyl-1,2,3,4-tetrahydroisoquinoline is 1:1-2, and 1:1.1-1.5 is preferred.

Method 2. The 4-chloro-2-(4-fluoroaniline)-5,6-dimethylpyrimidine (7) and 1-methyl-1,2,3,4-tetrahydroisoquinoline or hydrochloride thereof are heated to react in the solvent by adding base, after the reaction, water and dichloromethane are added into the reaction liquid, with stirring and separating the water layer, and the water layer is extracted with dichloromethane, the combined dichloromethane layer is washed with dilute hydrochloric acid and water, the dichloromethane layer is concentrated and the residues are dissolved in ethanol, hydrochloric acid is added to adjust pH to 1, crystallization is performed after stirring, and the revaprazan hydrochloride is obtained, wherein the feeding molar ratio of 4-chloro-2-(4-fluoroaniline)-5,6-dimethylpyrimidine (7) to 1-methyl-1,2,3,4-tetrahydroisoquinoline to the base can be 1:1-2:0-5, and 1:1.1-1.5:1-3 is preferred.

The 1-methyl-1,2,3,4-tetrahydroisoquinoline or hydrochloride thereof described in above-mentioned step (3) can be optical isomers thereof, namely (R)-(+)-1-methyl-1,2,3,4-tetrahydroisoquinoline or (S)-(−)-1-methyl-1,2,3,4-tetrahydroisoquinoline, and also can be hydrochloride thereof.

The solvent described in above-mentioned step (3) includes, but is not limited to one or more of ethylene glycol, glycerol, 1,2-propylene glycol, 1,3-propylene glycol, DMF (dimethylformamide), DMSO (dimethylsulfoxide), dimethylacetamide, N-methylpyrrolidone, ethylene glycol monomethyl ether and dioxane, and the ethylene glycol, glycerol and DMF are preferable solvents.

The feeding ratio by weight is 1:0.1-10, and 1:0.5-3 is preferred. The feeding ratio by weight refers to the weight ratio of 4-chloro-2-(4-fluoroaniline)-5,6-dimethylpyrimidine (7) to the solvent.

The reaction temperature is 100-180° C., and 120-140° C. is preferred.

The base described in above-mentioned step (3) includes, but is not limited to one or more or triethylamine, diisopropylethylamine, pyridine, 4-dimethylaminopyridine and N-methylmorpholine, and diisopropylethylamine is preferred.

The ethanol concentration described in above-mentioned step (3) is 10%-100%, and 50%-80% is preferred.

Beneficial Effects

1. Lowered Production Costs and Saved Reagents

In the preparation of 4-hydroxyl-2-(4-fluoroaniline)-5,6-dimethylpyrimidine (6) in step (1), the addition of organic base such as sodium alcoholate, pyridine and the like is not necessary for catalysis, the slow dropwise addition of 2-methyl ethyl acetoacetate is not necessary, and the evaporation of low-boiling point solvents is not necessary during reaction process.

Relatively highly-priced DMF is not used as solvent, the solvent (DMF, methanol and ethanol), which is miscible with water and difficult in reclaiming and reusing, is not used, and the employed solvent can be reclaimed and reused after simple treatment. The preparation of 4-chloro-2-(4-fluoroaniline)-5,6-dimethylpyrimidine (7) in step (2) only uses small amount of phosphorus oxychloride for reaction, and the employed solvent can be reclaimed and reused. The preparation of revaprazan hydrochloride in step (3) uses small amount of single solvent, and the addition of catalyst is not needed.

2. Simplified Preparation Method With Few Steps and Without Dropwise Addition of Materials at a High Temperature In the preparation of 4-hydroxyl-2-(4-fluoroaniline)-5,6-dimethylpyrimidine (6) in step (1), it is only required to separate out the moisture generated from the reaction, the filtration of the generated salt while hot is not necessary, and the adjustment of pH value is also not necessary.

When reaction is completed, it is only required to filter the product; in the preparation of 4-chloro-2-(4-fluoroaniline)-5,6-dimethylpyrimidine (7) in step (2), the materials are added into the reactor at room temperature, and the dropwise addition of phosphorus oxychloride at high temperature of 85° C. is not necessary. The adjustment of pH value of the reaction liquid to higher than 10 is not necessary, and wrapping of phosphate into the product is avoided; in the preparation process of revaprazan in step (3), under the condition of catalysis without the base, when the reaction is completed, the hydrochloric acid is directly added to form salt after diluted with addition of ethanol, which simplifies the process and is more suitable for industrialized production; under the condition of adding the base, it is only required to neutralize excessive base with dilute acid, washing the dichloromethane solution with base is not necessary, and the processing step is simplified.

3. Shortened Reaction Time

Due to the fact that mixed solvent and base with low boiling point are not used in the preparation of revaprazan hydrochloride in step (3), reaction time is significantly shortened so as to further shorten the overall reaction time.

4. Improved Product Purity

In the preparation of 4-chloro-2-(4-fluoroaniline)-5,6-dimethylpyrimidine (7) in step (2), due to the fact that the product is dissolved in organic solvent, the phosphate generated after reaction of phosphorus oxychloride is dissolved in water so as to be separated, which avoids wrapping large amount of phosphate into the product; in the preparation of 4-hydroxyl-2-(4-fluoroaniline)-5,6-dimethylpyrimidine (6) in step (1), the preparation of 4-chloro-2-(4-fluoroaniline)-5,6-dimethylpyrimidine (7) in step (2) and the preparation of revaprazan hydrochloride in step (3), the purities of the prepared products all reach higher than 99%, and the character of the final product is white powder.

BRIEF DESCRIPTION OF THE DRAWINGS

FIG. 1. Synthetic route map of revaprazan hydrochloride

DETAILED DESCRIPTION OF THE INVENTION

The following embodiments are used to further illustrate the present invention, but not intended to further limit the present invention.

Embodiment 1: Preparation of Revaprazan Hydrochloride

1. Preparation of 4-hydroxyl-2-(4-fluoroaniline)-5,6-dimethylpyrimidine

The preparation step includes under the protection of nitrogen, successively adding 368 g of toluene, 18.4 g of 4-fluorophenyl guanidine carbonate (1:0.5) and 14.4 g of 2-methyl ethyl acetoacetate into a reactor, stirring and heating until systematic reflux, keeping the water diversion state of reflux until reaction completion, lowering the temperature, adding water and stirring for 30 min, and then obtaining 20.1 g of the white solid powder after filtering, washing filter cake with water and drying. The yield of product is 86.3%.

2. Preparation of 4-chloro-2-(4-fluoroaniline)-5,6-dimethylpyrimidine

The preparation step includes under the protection of nitrogen, successively adding 18.6 g of 4-hydroxyl-2-(4-fluoroaniline)-5,6-dimethylpyrimidine and 372 g of chlorobenzene into a reactor, adding 6.1 g of phosphorus oxychloride while stirring, heating to raise the temperature until reflux, keeping the state of reflux is until reaction completion, lowering the temperature, adding iced water, separating the liquid, extracting the water layer with chlorobenzene for twice and combining the organic layers, and then obtaining 17.8 g of pale yellow solid powder after washing with water and concentrating under reduced pressure to dryness. The yield is 88.6%.

3. Preparation of Revaprazan Hydrochloride

The preparation step includes under the protection of nitrogen, successively adding 15.1 g of 4-chloro-2-(4-fluoroaniline)-5,6-dimethylpyrimidine, 8.9 g of (S)-(–)-1-methyl-1,2,3,4-tetrahydroisoquinoline, 30.3 g of triethylamine and 45 g of ethylene glycol monomethyl ether into a reactor and stirring, heating and reacting at 100-110° C., after reaction completion, cooling to room temperature, adding dichloromethane and water, separating the water layer and extracting with dichloromethane, washing the dichloromethane layer with dilute hydrochloric acid and water, concentrating the dichloromethane layer, and dissolving the residues with addition of ethanol, adjusting pH to 1 with addition of hydrochloric acid, and then obtaining 20.4 g of white powder after stirring, cooling and filtering. The yield of product is 85.4%.

Embodiment 2: Preparation of Revaprazan Hydrochloride

1. Preparation of 4-hydroxyl-2-(4-fluoroaniline)-5,6-dimethylpyrimidine

The preparation step includes under the protection of nitrogen, successively adding 184 g of toluene, 36.8 g of 4-fluorophenyl guanidine carbonate (1:0.5), 34.6 of 2-methyl ethyl acetoacetate and 7.6 g of sodium hydroxide into a reactor, stirring and heating until systematic reflux, keeping the water diversion state of reflux until reaction completion, lowering the temperature, adding water and stirring for 30 min, and then obtaining 40.8 g of the white solid powder after filtering, washing filter cake with water and drying. The yield of product is 87.6%.

2. Preparation of 4-chloro-2-(4-fluoroaniline)-5,6-dimethylpyrimidine

The preparation step includes under the protection of nitrogen, successively adding 23.3 g of 4-hydroxyl-2-(4-fluoroaniline)-5,6-dimethylpyrimidine and 117 g of toluene in a reactor, adding 10.7 g of phosphorus oxychloride while stirring, heating to raise the temperature till reflux, keeping the state of reflux until the reaction completion, cooling, adding ice water, then dropwise adding a sodium hydroxide aqueous solution to adjust pH to 4, performing liquid separation, extracting the water layer twice with toluene, combining the organic layers, washing with water, and concentrating under reduced pressure to dryness to obtain 22.3 g of pale yellow solid powder. The yield is 88.6%.

3. Preparation of Revaprazan Hydrochloride

The preparation step includes under the protection of nitrogen, successively adding 20.1 g of 4-chloro-2-(4-fluoroaniline)-5,6-dimethylpyrimidine, 14.1 g of 1-methyl-1,2,3,4-tetrahydroisoquinoline and 16 g of ethylene glycol in a reactor, stirring and heating for reaction at 120-130° C., cooling after the reaction, and adding 70% of ethanol. Then adding hydrochloric acid to adjust pH to 1, stirring and cooling to room temperature, filtering, washing the filter cake with water, and washing with 70% of ethanol to obtain 28.7 g of white powder, and the product yield is 89.9%.

Embodiment 3: Preparation of Revaprazan Hydrochloride

1. Preparation of 4-hydroxyl-2-(4-fluoroaniline)-5,6-dimethylpyrimidine

The preparation step includes under the protection of nitrogen, successively adding 147 g of toluene, 36.8 g of 4-fluorophenyl guanidine carbonate (1:0.5), 40.4 g of 2-methyl ethyl acetoacetate and 11.2 g of potassium hydroxide in a reactor, stirring and heating till systematic reflux, keeping the reflux and water segregation state until reaction completion, cooling, adding water, stirring for 30 minutes, filtering, washing the filter cake with water and drying to obtain 40.6 g of white solid powder. The product yield is 87.1%.

2. Preparation of 4-chloro-2-(4-fluoroaniline)-5,6-dimethylpyrimidine

The preparation step includes under the protection of nitrogen, successively adding 35.0 g of 4-hydroxyl-2-(4-fluoroaniline)-5,6-dimethylpyrimidine and 105 g of toluene in the reactor, adding 13.8 g of phosphorus oxychloride while stirring, heating to raise the temperature till reflux, keeping the state of reflux until reaction completion, cooling, adding ice water, then dropwise adding a sodium hydroxide aqueous solution to adjust pH to 1, performing liquid separation, extracting the water layer twice with toluene, combining the organic layers, washing with water, and concentrating under reduced pressure to dryness to obtain 33.9 g of pale yellow solid powder. The yield is 89.7%.

3. Preparation of Revaprazan Hydrochloride

The preparation step includes under the protection of nitrogen, successively adding 25.2 g of 4-chloro-2-(4-fluoroaniline)-5,6-dimethylpyrimidine, 23.9 g of (S)-(−)-1-methyl-1,2,3,4-tetrahydroisoquinoline hydrochloride and 250 g of glycerol in a reactor, stirring while heating for a reaction at 110-120° C., cooling after the reaction, and adding 50% of ethanol. Then adding hydrochloric acid to adjust pH to 1, stirring and cooling to room temperature, filtering, washing the filter cake with water, and washing with 50% of ethanol to obtain 35.9 g of white powder, and the product yield is 90.0%.

Embodiment 4: Preparation of Revaprazan Hydrochloride

1. Preparation of 4-hydroxyl-2-(4-fluoroaniline)-5,6-dimethylpyrimidine

The preparation step includes under the protection of nitrogen, successively adding 295 g of toluene, 36.8 g of 4-fluorophenyl guanidine carbonate (1:0.5), 43.2 g of 2-methyl ethyl acetoacetate and 17.2 g of barium hydroxide in a reactor, stirring and heating till systematic reflux, keeping the reflux and water segregation state until reaction completion, cooling, adding water, stirring for 30 minutes, filtering, washing the filter cake with water and drying to obtain 41.0 g of white solid powder. The product yield is 88.0%.

2. Preparation of 4-chloro-2-(4-fluoroaniline)-5,6-dimethylpyrimidine

The preparation step includes under the protection of nitrogen, successively adding 37.3 g of 4-hydroxyl-2-(4-fluoroaniline)-5,6-dimethylpyrimidine and 75 g of DMF in a reactor, adding 19.5 g of phosphorus oxychloride while stirring, heating to raise the temperature till reflux, keeping the state of reflux until reaction completion, cooling, adding toluene, adding ice water, then dropwise adding a sodium hydroxide aqueous solution to adjust pH to 2, performing liquid separation, extracting the water layer twice with toluene, combining the organic layers, washing with water, and concentrating under reduced pressure to dryness to obtain 35.8 g of pale yellow solid powder. The yield is 88.8%.

3. Preparation of Revaprazan Hydrochloride

The preparation step includes under the protection of nitrogen, successively adding 35.2 g of 4-chloro-2-(4-fluoroaniline)-5,6-dimethylpyrimidine and 24.7 g of 1-methyl-1,2,3,4-tetrahydroisoquinoline, 27.1 g of diisopropylethylamine and 1,2-propylene glycol in a reactor, stirring while heating for reaction at 130-140° C., after the reaction, cooling to room temperature, adding dichloromethane and water, separating out a water layer, extracting the water with dichloromethane, washing the dichloromethane layer with dilute hydrochloric acid and water, concentrating the dichloromethane layer, dissolving the residues in ethanol, then adding hydrochloric acid to adjust pH to 1, stirring, cooling, and filtering to obtain 47.8 g of white powder, and the product yield is 85.7%.

Embodiment 5: Preparation of Revaprazan Hydrochloride

1. Preparation of 4-hydroxyl-2-(4-fluoroaniline)-5,6-dimethylpyrimidine

The preparation step includes under the protection of nitrogen, successively adding 129 g of toluene, 64.5 g of 4-fluorophenyl guanidine carbonate (1:1), 56.1 g of 2-methyl ethyl acetoacetate and 7.2 g of lithium hydroxide in a reactor, stirring and heating till systematic reflux, keeping the reflux and water segregation state until reaction completion, cooling, adding water, stirring for 30 minutes, filtering, washing the filter cake with water and drying to obtain 59.7 g of white solid powder. The product yield is 85.3%.

2. Preparation of 4-chloro-2-(4-fluoroaniline)-5,6-dimethylpyrimidine

The preparation step includes under the protection of nitrogen, successively adding 46.6 g of 4-hydroxyl-2-(4-fluoroaniline)-5,6-dimethylpyrimidine and 186 g of xylene in a reactor, adding 27.6 g of phosphorus oxychloride with stirring, heating to raise the temperature till reflux, keeping the state of reflux until of reaction completion, cooling, adding ice water, then adding dropwise a potassium hydroxide aqueous solution to adjust pH to 2, performing liquid separation, extracting the water layer twice with xylene, combining the organic layers, washing with water, and concentrating under reduced pressure to dryness to obtain 44.2 g of pale yellow solid powder. The yield is 87.9%.

3. Preparation of Revaprazan Hydrochloride

The preparation step includes under the protection of nitrogen, successively adding 40.3 g of 4-chloro-2-(4-fluoroaniline)-5,6-dimethylpyrimidine, 25.8 g of 1-methyl-1,2,3,4-tetrahydroisoquinoline and 40 g of 1,3-propanediol in a reactor, stirring and heating for reacting at 140-150° C., cooling after the reaction, and adding ethanol. Then adding hydrochloric acid to adjust pH to 1, stirring and cooling down to room temperature, filtering, washing the filter cake with water and washing with ethanol to obtain 57.1 g of white powder, the product yield being 89.5%.

Embodiment 6: Preparation of Revaprazan Hydrochloride

1. Preparation of 4-hydroxyl-2-(4-fluoroaniline)-5,6-dimethylpyrimidine

The preparation step includes under the protection of nitrogen, successively adding 430 g of benzene, 43.0 g of 4-fluorophenyl guanidine carbonate (1:1), 46.2 g of 2-methyl ethyl acetoacetate and 42.4 g of sodium carbonate in a reactor, stirring and heating till systematic reflux, keeping the reflux and water segregation state until reaction completion, cooling, adding water, stirring for 30 minutes, filtering, washing the filter cake with water and drying to obtain 40.8 g of white solid powder. The product yield is 87.6%.

2. Preparation of 4-chloro-2-(4-fluoroaniline)-5,6-dimethylpyrimidine

The preparation step includes under the protection of nitrogen, successively adding 23.3 g of 4-hydroxyl-2-(4-fluoroaniline)-5,6-dimethylpyrimidine and 93 g of benzene in a reactor, adding 15.3 g of phosphorus oxychloride with stirring, heating to raise temperature till reflux, keeping the state of reflux until reaction completion, cooling, adding ice water, then dropwise adding a potassium hydroxide aqueous solution to adjust pH to 5, performing liquid separation, extracting the water layer twice with benzene, combining the organic layers, washing with water, and concentrating under reduced pressure to dryness to obtain 21.9 g of pale yellow solid powder. The yield is 87.0%.

3. Preparation of Revaprazan Hydrochloride

The preparation step includes under the protection of nitrogen, successively adding 20.1 g of 4-chloro-2-(4-fluoroaniline)-5,6-dimethylpyrimidine, 17.7 g of (R)-(+)-1-methyl-1,2,3,4-tetrahydroisoquinoline and 2 g of DMF in a reactor, stirring and heating for reacting at 140-150° C., cooling after the reaction, and adding 10% ethanol. Then adding hydrochloric acid to adjust pH to 1, stirring and cooling down to room temperature, filtering, washing the filter cake with water and washing with 10% ethanol to obtain 28.3 g of white powder, the product yield being 88.7%.

Embodiment 7: Preparation of Revaprazan Hydrochloride

1. Preparation of 4-hydroxyl-2-(4-fluoroaniline)-5,6-dimethylpyrimidine

The preparation step includes under the protection of nitrogen, successively adding 516 g of chlorobenzene, 64.5 g of 4-fluorophenyl guanidine carbonate (1:1), 86.4 g of 2-methyl ethyl acetoacetate and 15.4 g of sodium methylate in a reactor, stirring and heating till systematic reflux, keeping the reflux and water segregation state until reaction completion, cooling, adding water, stirring for 30 minutes, filtering, washing the filter cake with water and drying to obtain 61.9 g of white solid powder. The product yield is 88.5%.

2. Preparation of 4-chloro-2-(4-fluoroaniline)-5,6-dimethylpyrimidine

The preparation step includes under the protection of nitrogen, successively adding 46.6 g of 4-hydroxyl-2-(4-fluoroaniline)-5,6-dimethylpyrimidine and 233 g of cyclohexane in a reactor, adding 36.6 g of phosphorus oxychloride with stirring, heating to raise the temperature till reflux, keeping the state of reflux until reaction completion, cooling, adding ice water, then dropwise adding a barium hydroxide aqueous solution to adjust pH to 7, performing liquid separation, extracting the water layer twice with cyclohexane, combining the organic layers, washing with water, and concentrating under reduced pressure to dryness to obtain 45.0 g of pale yellow solid powder. The yield is 89.5%.

3. Preparation of Revaprazan Hydrochloride

The preparation step includes under the protection of nitrogen, successively adding 40.3 g of 4-chloro-2-(4-fluoroaniline)-5,6-dimethylpyrimidine, 35.3 g of 1-methyl-1,2,3,4-tetrahydroisoquinoline and 20 g of DMSO in a reactor, stirring and heating for reaction at 150-160° C., cooling after the reaction, and adding 80% ethanol. Then adding hydrochloric acid to adjust pH to 1, stirring and cooling down to room temperature, filtering, washing the filter cake with water and washing with 80% ethanol, to obtain 57.2 g of white powder, and the product yield being 89.7%.

Embodiment 8: Preparation of Revaprazan Hydrochloride

1. Preparation of 4-hydroxyl-2-(4-fluoroaniline)-5,6-dimethylpyrimidine

The preparation step includes successively adding 150 g of cyclohexane, 21.5 g of 4-fluorophenyl guanidine carbonate (1:1), 18.7 g of 2-methyl ethyl acetoacetate and 3.4 g of sodium ethoxide in a reactor, stirring and heating till systematic reflux, keeping the reflux and water segregation state until the reaction completion, cooling, adding water, stirring for 30 minutes, filtering, washing the filter cake with water and drying to obtain 20.2 g of white solid powder. The product yield is 86.7%.

2. Preparation of 4-hydroxyl-2-(4-fluoroaniline)-5,6-dimethylpyrimidine

The preparation step includes successively adding 11.6 g of 4-hydroxyl-2-(4-fluoroaniline)-5,6-dimethylpyrimidine and 116 g of n-hexane in a reactor, adding 15.3 g of phosphorus oxychloride while stirring, heating to raise the temperature till reflux, keeping the state of reflux until the reaction completion, cooling, adding ice water, then dropwise adding a barium hydroxide aqueous solution to adjust pH to 10, performing liquid separation, extracting the water layer twice with the n-hexane, combining the organic layers, washing with water, and concentrating under reduced pressure to dryness to obtain 11.0 g of pale yellow solid powder. The yield is 87.3%.

3. Preparation of Revaprazan Hydrochloride

The preparation step includes successively adding 10.1 g of 4-chloro-2-(4-fluoroaniline)-5,6-dimethylpyrimidine and 14.7 g of (R)-(+)-1-methyl-1,2,3,4-tetrahydroisoquinoline, 9.48 g of pyridine and 10 g of 1,4-dioxane in a reactor, stirring and heating for reaction at 100-110° C., cooling to room temperature after the reaction, adding dichloromethane and water, separating out a water layer, extracting the water layer with dichloromethane, washing the dichloromethane layer with dilute hydrochloric acid and water, concentrating the dichloromethane layer, dissolving the residues in ethanol, then dropwise adding hydrochloric acid to adjust pH to 1, stirring, cooling, and filtering to obtain 13.6 g of white solid powder, and the product yield is 85.1%.

Embodiment 9: Preparation of Revaprazan Hydrochloride

1. Preparation of 4-hydroxyl-2-(4-fluoroaniline)-5,6-dimethylpyrimidine

The preparation step includes successively adding 184 g of toluene, 18.4 g of 4-fluorophenyl guanidine carbonate (1:0.5), 18.7 g of 2-methyl ethyl acetoacetate and 13.8 g of potassium carbonate in a reactor, stirring and heating till systematic reflux, keeping the reflux and water segregation state until reaction completion, cooling, adding water, stirring for 30 minutes, filtering, washing the filter cake with water and drying to obtain 19.8 g of white solid powder. The product yield is 85.0%.

2. Preparation of 4-chloro-2-(4-fluoroaniline)-5,6-dimethylpyrimidine

The preparation step includes successively adding 18.6 g of 4-hydroxyl-2-(4-fluoroaniline)-5,6-dimethylpyrimidine and 93 g of toluene in a reactor, adding 8.6 g of phosphorus oxychloride while stirring, heating to raise the temperature till reflux, keeping the state of reflux until reaction completion, cooling, adding ice water, then dropwise adding a sodium hydroxide aqueous solution to adjust pH to 4, performing liquid separation, extracting the water layer twice with the toluene, combining the organic layers, washing with water, and concentrating under reduced pressure to dryness to obtain 17.8 g of pale yellow solid powder. The yield is 88.6%.

3. Preparation of Revaprazan Hydrochloride

The preparation step includes successively adding 15.1 g of 4-chloro-2-(4-fluoroaniline)-5,6-dimethylpyrimidine and 10.4 g of 1-methyl-1,2,3,4-tetrahydroisoquinoline, 10.3 g of 4-dimethylaminopyridine and 10.6 g of dimethylacetamide in a reactor, stirring while heating for reaction at 115-125° C., cooling to room temperature after the reaction, adding dichloromethane and water, separating out a water layer, extracting the water layer with dichloromethane, washing the dichloromethane layer with dilute hydrochloric acid and water, concentrating the dichloromethane layer, dissolving the residues in ethanol, then adding hydrochloric acid to adjust pH to 1, stirring, cooling, and filtering to obtain 20.3 g of white solid powder, and the product yield is 84.9%.

Embodiment 10: Preparation of Revaprazan Hydrochloride

1. Preparation of 4-hydroxyl-2-(4-fluoroaniline)-5,6-dimethylpyrimidine

The preparation step includes under the protection of nitrogen, successively adding 147 g of toluene, 18.4 g of 4-fluorophenyl guanidine carbonate (1:0.5), 20.2 g of 2-methyl ethyl acetoacetate and 7.4 g of lithium carbonate in a reactor, stirring and heating till systematic reflux, keeping the reflux and water segregation state until reaction completion, cooling, adding water, stirring for 30 minutes, filtering, washing the filter cake with water and drying to obtain 19.7 g of white solid powder. The product yield is 84.5%.

2. Preparation of 4-chloro-2-(4-fluoroaniline)-5,6-dimethylpyrimidine

The preparation step includes under the protection of nitrogen, successively adding 18.6 g of 4-hydroxyl-2-(4-fluoroaniline)-5,6-dimethylpyrimidine and 112 g of toluene in a reactor, adding 9.8 g of phosphorus oxychloride while stirring, heating to raise the temperature till reflux, keeping the state of reflux until reaction completion, cooling, adding ice water, then dropwise adding a sodium hydroxide aqueous solution to adjust pH to 5, performing liquid separation, extracting the water layer twice with the toluene, combining the organic layers, washing with water, and concentrating under reduced pressure to dryness to obtain 17.9 g of pale yellow solid powder. The yield is 89.0%.

3. Preparation of Revaprazan Hydrochloride

The preparation step includes successively adding 15.1 g of 4-chloro-2-(4-fluoroaniline)-5,6-dimethylpyrimidine and 11.3 g of 1-methyl-1,2,3,4-tetrahydroisoquinoline, 7.9 g of N-methylmorpholine and 10 g of N-methylpyrrolidone in a reactor, stirring and heating for reaction at 120-130° C., cooling to room temperature after the reaction, adding dichloromethane and water, separating out a water layer, extracting the water layer with dichloromethane, washing the dichloromethane layer with dilute hydrochloric acid and water, concentrating the dichloromethane layer, dissolving the residues in ethanol, then adding hydrochloric acid to adjust pH to 1, stirring, cooling, and filtering to obtain 20.4 g of white powder, and the product yield is 85.4%.

The invention claimed is:

1. A method for preparing revaprazan hydrochloride, comprising the following steps:
   (1) preparation of preparing 4-hydroxyl-2-(4-fluoroaniline)-5,6-dimethylpyrimidine: by adding 4-fluorophenyl guanidine carbonate and 2-methyl ethyl acetoacetate in a reactor, adding a solvent, adding a base or strong base salt or not adding base, carrying out reflux dehydration by heating until the raw materials are fully reacted, cooling, adding water, stirring, filtering, and washing with water to obtain 4-hydroxyl-2-(4-fluoroaniline)-5,6-dimethylpyrimidine;
   (2) preparation of 4-chloro-2-(4-fluoroaniline)-5,6-dimethylpyrimidine: by refluxing 4-hydroxyl-2-(4-fluoroaniline)-5,6-dimethylpyrimidine by heating with phosphorus oxychloride in a solvent until the raw materials are fully reacted, cooling, adding water, directly separating the liquid or separating the liquid after adjusting the pH with base, extracting the water layer with a solvent, combining the organic layers, and washing the organic layers with water until they are neutral, and concentrating the organic layer to obtain 4-chloro-2-(4-fluoroaniline)-5,6-dimethylpyrimidine;
   (3) preparation of preparing revaprazan hydrochloride: by heating 4-chloro-2-(4-fluoroaniline)-5,6-dimethylpyrimidine and 1-methyl-1,2,3,4-tetrahydroisoquinoline or hydrochloride salt thereof in a solvent until the raw materials are fully reacted, cooling, adding ethanol and hydrochloric acid, and filtering to obtain revaprazan hydrochloride, or adding base into 4-chloro-2-(4-fluoroaniline)-5,6-dimethylpyrimidine and 1-methyl-1,2,3,4-tetrahydroisoquinoline, heating in a solvent until the raw materials are fully reacted, adding water and dichloromethane, separating out water layers and extracting the water layer with dichloromethane, washing the combined dichloromethane layer with dilute hydrochloric acid and water, concentrating the dichlormethane layer, dissolving the residues into ethanol, adding hydrochloric acid for adjusting pH to 1, stirring and carrying out crystallization to obtain revaprazan hydrochloride.

2. The preparation method of claim 1, wherein the added base or strong base salt in step (1) is one or more of sodium hydroxide, potassium hydroxide, barium hydroxide, lithium hydroxide, sodium carbonate, potassium carbonate, lithium carbonate, sodium methoxide or sodium ethoxide, wherein molar feeding ratio of 4-fluorophenyl guanidine carbonate: 2-methyl ethyl acetoacetate: base is 1:1-2:0-2;

or the base is not added, wherein molar feeding ratio of 4-fluorophenyl guanidine carbonate and 2-methyl ethyl acetoacetate is 1:1-2.

3. The preparation method of claim 1, wherein the 4-fluorophenyl guanidine carbonate in step (1) is:
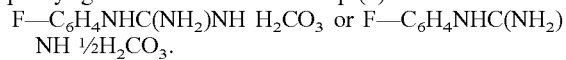
F—C$_6$H$_4$NHC(NH$_2$)NH H$_2$CO$_3$ or F—C$_6$H$_4$NHC(NH$_2$)NH ½H$_2$CO$_3$.

4. The preparation method of claim 1, wherein the solvent in step (1) is selected from one or more of toluene, xylene, benzene, chlorobenzene and cyclohexane, the feeding ratio by weight is 1:2-20.

5. The preparation method of claim 1, wherein the feeding molar ratio of 4-hydroxyl-2-(4-fluoroaniline)-5,6-dimethylpyrimidine:phosphorus oxychloride in step (2) is 1:0.5-2.

6. The preparation method of claim 1, wherein the solvent in the step (2) is selected from one or more of toluene, xylene, benzene, chlorobenzene, cyclohexane, n-hexane and DMF, and the feeding ratio by weight of 4-hydroxyl-2-(fluoroaniline)-5,6-dimethylpyrimidine to the solvent is 1:2-20.

7. The preparation method of claim 1, wherein adjusting the pH with the base in step (2) is such that the base is one or more of sodium hydroxide, potassium hydroxide and barium hydroxide, and the adjusted pH value is 1-10.

8. The preparation method of claim 1, wherein the 4-chloro-2-(4-fluoroaniline)-5,6-dimethylpyrimidine and 1-methyl-1,2,3,4-tetrahydroisoquinoline or hydrochloride salt thereof are reacted by heating in a solvent in step (3), and after the reaction, ethanol and hydrochloric acid are added to obtain the revaprazan hydrochloride, wherein the feeding molar ratio of the 4-chloro-2-(4-fluoroaniline)-5,6-dimethylpyrimidine: 1-methyl-1,2,3,4-tetrahydroisoquinoline or hydrochloride thereof is 1:1-2; or base is added into the 4-chloro-2-(4-fluoroaniline)-5,6-dimethylpyrimidine and 1-methyl-1,2,3,4-tetrahydroisoquinoline, followed by heating for reaction in a solvent, and after the reaction, cooling slightly, adding water and dichloromethane into the reaction liquid, stirring, separating the water layer and extracting the water layer with dichloromethane, washing the combined dichloromethane layer with dilute hydrochloric acid and water, concentrating the dichloromethane layer, dissolving the residue into ethanol, adding hydrochloric acid and adjusting the pH to 1, stirring and carrying out crystallization, to obtain revaprazan hydrochloride, wherein the feeding molar ratio of 4-chloro-2-(4-fluoroaniline)-5,6-dimethylpyrimidine: 1-methyl-1,2,3,4-tetrahydroisoquinoline or hydrochloride thereof: base is 1:1-2:0-5.

9. The preparation method of claim 1 wherein the base in step (3) is one or more of triethylamine, diisopropylethylamine, pyridine, 4-dimethylaminopyridine, and N-methylmorpholine.

10. The preparation method of claim 8, wherein the concentration of ethanol is 10%-100%.

11. The preparation method of claim 8, wherein the 1-methyl-1,2,3,4-tetrahydroisoquinoline or hydrochloride thereof can be one of (R)-(+)-1-methyl-1,2,3,4-tetrahydroisoquinoline, (S)-(−)-1-methyl-1,2,3,4-tetrahydroisoquinoline, and their hydrochlorides.

12. The preparation method of claim 8, wherein the solvent in step (3) can be one or more of ethylene glycol, glycerol, 1,2-propylene glycol, 1,3-propylene glycol, DMF (dimethylformamide), DMSO (dimethyl sulfoxide), dimethylacetamide, N-methyl pyrrolidinone, ethylene glycol monomethyl ether and dioxane, and the feeding ratio by weight is 1:0.1-10, and the reaction temperature is 100-180° C.

13. The preparation method of claim 1, wherein the reactions in the steps (1)-(3) are carried out under the protection of gas.

14. The preparation method of claim 2, wherein the 4-fluorophenyl guanidine carbonate in step (1) is:
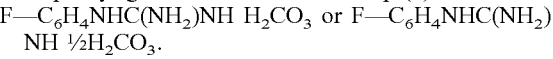
F—C$_6$H$_4$NHC(NH$_2$)NH H$_2$CO$_3$ or F—C$_6$H$_4$NHC(NH$_2$) NH ½H$_2$CO$_3$.

15. The preparation method of claim 8, wherein the base in step (3) is one or more of triethylamine, diisopropylethylamine, pyridine, 4-dimethylaminopyridine, and N-methylmorpholine.

16. A method for preparing revaprazan hydrochloride comprising the steps of:
  (1) reacting 4-fluorophenyl guanidine carbonate and 2-methyl ethyl acetoacetate under heated reflux in the presence of a solvent to obtain 4-hydroxyl-2-(4-fluoroaniline)-5,6-dimethylpyrimidine;
  (2) reacting the 4-hydroxyl-2-(4-fluoroaniline)-5,6-dimethylpyrimidine produced in step (1) with phosphorus oxychloride under reflux, and in the presence of a solvent, to obtain 4-chloro-2-(4-fluoroaniline)-5,6-dimethylpyrimidine;
  (3) reacting the 4-chloro-2-(4-fluoroaniline)-5,6-dimethylpyrimidine produced in step (2) with 1-methyl-1,2,3,4-tetrahydroisoquinoline or a hydrochloride salt thereof, in the presence of a solvent, thus obtaining revaprazan hydrochloride.

17. The preparation method of claim 1, wherein in step (1),
  the reaction is carried out in the presence of a base selected from the group consisting of sodium hydroxide, potassium hydroxide, barium hydroxide, lithium hydroxide, sodium carbonate, potassium carbonate, lithium carbonate, sodium methoxide, sodium ethoxide, and combinations thereof and wherein molar feeding ratio of 4-fluorophenyl guanidine carbonate to 2-methyl ethyl acetoacetate to base is in the range of 1:1.2-1.6:0.5-1, or the base is not added; and, wherein molar feeding ratio of 4-fluorophenyl guanidine carbonate to 2-methyl ethyl acetoacetate is in the range of 1:1.2-1.6.

18. The preparation method of claim 1, wherein the molar feeding ratio of 4-hydroxyl-2-(4-fluoroaniline)-5,6-dimethylpyrimidine to phosphorus oxychloride in step (2) is in the range of 1:0.6-1.0.

19. The preparation method of claim 1, wherein the 4-chloro-2-(4-fluoroaniline)-5,6-dimethylpyrimidine and 1-methyl-1,2,3,4-tetrahydroisoquinoline or hydrochloride salt thereof are reacted by heating in a solvent in step (3), and after the reaction, ethanol and hydrochloric acid are added to obtain the revaprazan hydrochloride, wherein the molar feeding ratio of the 4-chloro-2-(4-fluoroaniline)-5,6-dimethylpyrimidine to 1-methyl-1,2,3,4-tetrahydroisoquinoline or hydrochloride thereof is in the range of 1:1-2; or base is added into the 4-chloro-2-(4-fluoroaniline)-5,6-dimethylpyrimidine and 1-methyl-1,2,3,4-tetrahydroisoquinoline reaction mixture, followed by heating the reaction mixture in the presence of a solvent, and after the reaction, purifying the product to obtain revaprazan hydrochloride, and wherein the molar feeding ratio of 4-chloro-2-(4-fluoroaniline)-5,6-dimethylpyrimidine to 1-methyl-1,2,3,4-tetrahydroisoquinoline, or hydrochloride thereof, to base is in the range of 1:1-2:0-5.

20. The preparation method of claim 8, wherein the solvent in step (3) is selected from the group consisting of ethylene glycol, glycerol, 1,2-propylene glycol, 1,3-propylene glycol, dimethylformamide, dimethyl sulfoxide, dimethylacetamide, N-methyl pyrrolidinone, ethylene glycol monomethyl ether, dioxane, and combinations thereof, and the feeding ratio by weight is in the range of from 1:0.1-10, and where the reaction temperature is from about 100° C. to about 180° C.

21. The method of claim 1 wherein step (1) is conducted with no adjustment of the pH value.

22. The method of claim 1 wherein step (1) the methyl ethyl acetoacetate is not added drop-wise.

23. The method of claim 1 wherein step (1) the solvent is in the absence of DMF, methanol and ethanol.

24. The method of claim 1 wherein step (2) the reactants are added at room temperature.

25. The method of claim 1 wherein step (2) the phosphorous oxychloride is not added drop-wise.

26. The method of claim 1 wherein step (3) the addition of base changes the pH to a pH of 10 or less.

27. The method of claim 1 wherein step (3) employs a single solvent.

28. The method of claim 1 wherein step (3) base is not used.

29. The method of claim 1 wherein one or more of steps (1), (2) or (3) result in a product purity of that step of greater than 99%.

30. A method for preparing revaprazan hydrochloride, comprising the following steps:

(1) preparation of preparing 4-hydroxyl-2-(4-fluoroaniline)-5,6-dimethylpyrimidine: by adding 4-fluorophenyl guanidine carbonate and 2-methyl ethyl acetoacetate in a reactor, wherein the 2-methyl ethyl acetoacetate is not added drop-wise, adding a solvent which is not DMF, methanol or ethanol, not adjusting the pH and carrying out reflux dehydration by heating until the raw materials are fully reacted, cooling, adding water, stirring, filtering, and washing with water to obtain 4-hydroxyl-2-(4-fluoroaniline)-5,6-dimethylpyrimidine;

(2) preparation of 4-chloro-2-(4-fluoroaniline)-5,6-dimethylpyrimidine: by refluxing room temperature 4-hydroxyl-2-(4-fluoroaniline)-5,6-dimethylpyrimidine by heating with room temperature phosphorus oxychloride in a solvent wherein the phosphorus oxychloride is not added drop-wise, until the raw materials are fully reacted, cooling, adding water, directly separating the liquid or separating the liquid after adjusting the pH with base, extracting the water layer with a solvent, combining the organic layers, and washing the organic layers with water until they are neutral, and concentrating the organic layer to obtain 4-chloro-2-(4-fluoroaniline)-5,6-dimethylpyrimidine;

(3) preparation of preparing revaprazan hydrochloride: by heating 4-chloro-2-(4-fluoroaniline)-5,6-dimethylpyrimidine and 1-methyl-1,2,3,4-tetrahydroisoquinoline or hydrochloride salt thereof in a single solvent, in the absence of a base, until the raw materials are fully reacted, cooling, adding ethanol and hydrochloric acid, and filtering to obtain revaprazan hydrochloride, or adding base into 4-chloro-2-(4-fluoroaniline)-5,6-dimethylpyrimidine and 1-methyl-1,2,3,4-tetrahydroisoquinoline, wherein the addition of the base raises the pH to 10 or less, heating in a single solvent until the raw materials are fully reacted, adding water and dichloromethane, separating out water layers and extracting the water layer with dichloromethane, washing the combined dichloromethane layer with dilute hydrochloric acid and water, concentrating the dichlormethane layer, dissolving the residues into ethanol, adding hydrochloric acid for adjusting pH to 1, stirring and carrying out crystallization to obtain revaprazan hydrochloride, and wherein one or more of steps (1), (2) and (3) produces a product with a purity of greater than 99%.

\* \* \* \* \*